United States Patent [19]

Dreyer

[11] Patent Number: 5,132,206
[45] Date of Patent: Jul. 21, 1992

[54] FLUORESCENT PIGMENTS FOR TAGGING BIOLOGICAL MOLECULES

[76] Inventor: William J. Dreyer, 960 San Pasqual, #302, Pasadena, Calif. 91106

[21] Appl. No.: 262,184

[22] Filed: Oct. 20, 1988

Related U.S. Application Data

[63] Continuation of Ser. No. 134,587, Dec. 15, 1987, abandoned, which is a continuation of Ser. No. 619,613, Jun. 11, 1984, abandoned.

[51] Int. Cl.$^5$ .............................................. C12Q 1/68
[52] U.S. Cl. .......................................... 435/6; 435/4; 435/7.95; 435/7.92; 435/7.93; 435/7.94; 436/501; 436/94; 436/518; 436/523; 436/532; 436/800; 436/805; 436/810; 436/818; 436/814; 935/76; 935/78
[58] Field of Search .................. 435/6, 803, 7, 4; 436/94, 501, 518, 523, 532, 4, 800, 805, 809, 810, 818, 814; 422/61; 935/78, 81, 76

[56] References Cited

U.S. PATENT DOCUMENTS

| | | |
|---|---|---|
| 2,809,954 | 10/1957 | Kazenas . |
| 4,059,407 | 11/1977 | Hochstrasser . |
| 4,108,972 | 8/1978 | Dreyer . |
| 4,216,245 | 8/1980 | Johnson . |
| 4,261,968 | 4/1981 | Ullman .............................. 436/800 X |
| 4,358,535 | 11/1982 | Falkow et al. . |
| 4,385,126 | 5/1983 | Chen . |
| 4,496,658 | 1/1985 | Kondo et al. . |
| 4,563,419 | 1/1986 | Ranki et al. .............................. 435/6 |

OTHER PUBLICATIONS

Voedisch, R. "Luminescent Pigments, Organic" In Pigment Handbook (Patten, ed.) 1973 pp. 891–901.

*Primary Examiner*—Amelia Burgess Yarbrough
*Attorney, Agent, or Firm*—Joseph E. Mueth

[57] ABSTRACT

A general method of assay for biological molecules using daylight fluorescent particles. The method described is applicable to assays involving immunological reagents, nucleic acids, hormones and neurotransmitters.

17 Claims, No Drawings

FLUORESCENT PIGMENTS FOR TAGGING BIOLOGICAL MOLECULES

This application is a continuation of application Ser. No. 134,587 filed Dec. 15, 1987 which was a continuation of Ser. No. 619,613 filed Jun. 11, 1987, both now abandoned.

BACKGROUND OF THE INVENTION

The present invention relates to the use of daylight fluorescent materials as labels for biological molecules. More specifically this invention involves the use of daylight fluorescent materials in assays for antigens, antibodies, receptors, and fragments of nucleic acid macromolecules with particular base sequences.

Living organisms produce a variety of macromolecules with the unusual property of reversible binding to a highly restricted group of other molecules. The bonds formed are of intermediate strength, involving hydrogen bonds, Van der Waals forces and hydrophobic interactions.

Recognition is a term which has been used to describe this general phenomenon. Recognition is utilized widely by the immune system. Receptors on the surfaces of somatic cells recognize the presence of minute quantities of hormones; receptors on neurons and muscle cells recognize neurotransmitters in tissue fluids. Interaction of complementary strands of nucleic acids and of enzymes and their substrates are further examples of this general phenomenon.

Increasingly, recognition has become the preferred method of detecting specific biological molecules for scientific and clinical applications. The specificity and sensitivity of these reactions is very high.

The most common method for detecting biological recognition is to label one of the reacting species with a radioactive isotope as in radioimmunoassays (RIA). This method is effective and is used widely, especially in research laboratories which have the specialized equipment for use and detection of radioisotopes. The health hazard and expense involved in the use of radioisotopes, however, have limited use of the method outside of the research laboratory.

One alternative to the use of radioisotopes as labels is to covalently bind certain enzymes capable of generating a colored species from a colorless substrate to one of the reacting molecules. Although methods involving enzyme labels are very sensitive, time, temperature, and other conditions must be scrupulously controlled in order to achieve accurate results. In addition, enzymes are prone to denaturation and degradation during storage.

Fluorescent labels provide a third alternative and are not subject to the above described limitations. With sophisticated equipment, very high sensitivity can be achieved (U.S. Pat. No. 4,261,968). But fluorescent labels are subject to bleaching over time and under ordinary conditions of measurement.

Therefore despite the advantages of existing methods of assay involving fluorescent labels, there is a need for simpler assay methods. This is particularly true where the assay is to be conducted in an environment where sophisticated instrumentation is unavailable, such as small clinics, the farm or the home. Accordingly, it is desirable to develop assay methods utilizing fluorescent labels which do not require the specialized light sources or detectors otherwise used in such assays. Ideally it is desirable to achieve quantitative or semi-quantitative results using conventional light sources and the unaided eye, in a manner analogous to the use of pH paper.

SUMMARY OF THE INVENTION

It has now been discovered that biological macromolecules labeled with particles exhibiting the property of daylight fluorescence fulfill the needs described above. These labels fluorescent in response to wavelengths contained in ordinary indoor light as well as sunlight. In addition they reflect a portion of the incident light in the same approximate wave-length as fluorescent emission occurs. Accordingly, the luminance of such pigments is greater than either fluorescence or ordinary reflective pigments. As an example, the luminance of a typical daylight fluorescent orange is approximately 55 percent of incident illumination, whereas a nonfluorescent pigment of the same color has a luminance of only approximately 15 percent (Voedisch, "Luminescent Pigments, Organic" in *Pigment Handbook* at 898 (Patten, ed. 1973)). Labels of this type are stable even under brilliant illumination, unlike ordinary fluorescent pigments.

Materials exhibiting the property of daylight fluorescence are available in a variety of sizes including particles with molecular dimensions. Together with their high luminance and resistance to bleaching, daylight fluorescent particles have properties which have made it possible to devise, not only extremely sensitive and simple methods of instrumental analysis, but have permitted the development of assays that can be carried out with the naked eye using ordinary illumination. The latter development opens up the possibility of performing sensitive assays at low cost in the home, farm, and clinical office environment.

DETAILED DESCRIPTION

Methods for preparing daylight fluorescent materials have been known for over 30 years (Luminescent Pigments, supra at 896). Briefly, the property of daylight fluorescence is achieved by creating a dilute solution of certain dyes, such as rhodamine, in a solid phase. A dilute solution is required in order to avoid quenching of the fluorescence emission. There are three methods for achieving the desired dispersion in a solid phase. The dye may be mixed with a resin matrix which is subsequently dried and ground to a powder (U.S. Pat. No. 2,809,954). Alternatively, the powdered resin may be colored in a dye bath (U.S. Pat. No. 2,938,873) or a resin precipitate may be formed in a dye bath (British Pat. No. 770,889, cited in Luminescent Pigments, supra at p. 899). Powders prepared according to these methods are readily available from commercial sources.

In order to achieve consistent results with the techniques described below, it is desirable to utilize dye particles of uniform size. To this end, commercially prepared powders are obtained which have been prepared to contain predominantly particles of the desired size. These may be further fractionated by commercial firms which provide particle fractionation services. Alternatively they are fractionated in aqueous suspension by conventional differential centrifugation. Extremely small particles are fractionated by means of gel permeation chromotography.

The second step in preparing daylight fluorescent materials for assays involves binding them to molecules which are to be used in the desired assay. Since the recognition-based assays considered here involve binding of the fluorescent molecules to be detected by molecules complementary to them, the molecules complementary to those which are to be detected are linked to the fluorescent particles.

There are two general approaches to bonding biochemicals, including macromolecules to small polymeric particles. First many molecules such as antibodies simply bind to hydrophobic surfaces by non-covalent forces. In one example, monoclonal antibodies in 0.1 normal sodium chloride solution are mixed with daylight fluorescent particles and allowed to stand in a cold room for one hour. Excess antibody is used to insure complete coating of the microparticles. This excess is removed by repeated centrifugation and washing of the particles by filtration through microporous filters which pass the antibody but not the particles. Separation may be effected by gel permeation chromotography. This approach is simple and often is adequate.

A second and generally more desirable approach involves covalent bonding of the compounds to particles. In general it is desirable to first add a chemical moiety which forms an "extension arm" to the microparticle surface before bonding any other species thereto. Di-aminoheptane and/or partially polymerized glutaraldehyde are added to the particles prior to attaching the biochemical of interest, in this method. This provides easier assess to the biochemical of interest by functional groups involved in these specific reactions. Several types of daylight fluorescent microparticles are available which contain hydroxyl or carboxyl groups on their surfaces.

In an example, di-aminoheptane or epsilonaminocaproic acid were bonded to microparticles using the aqueous carbodiimide reaction. See Molday, Dreyer, Rembaum and Yen, J. Cell. Biol., 64:75-88 (1975). After the coupling reaction was complete, excess reagents were removed by dialysis against 0.1 molar sodium cloride. Any of the biological probes discussed may then be easily bonded to these moieties using methods described below.

Many molecules which display specific recognition properties have primary amino groups available which can be used to couple these molecules to reactive microparticles. Almost all proteins and peptides can be bonded by means of such amino groups. Nucleic acid probes can now be automatically synthesized with one or more primary amino groups incorporated at the end of the polynucleotide sequence.

One convenient and effective means for coupling such molecules to microparticles which also have exposed primary amino groups involves the use of the bifunctional reagent glutaraldehyde, Molday et al., supra., and Rembaum, Yen, Cheong, Wallace, Molday, Gordon, and Dreyer, *Macromolecules*, 9:328-336 (1976). Briefly, an aqueous glutaraldehyde solution is added slowly to a suspension of microparticles in 0.1 molar sodium phosphate buffer at pH 7.0. The final concentration of glutaraldehyde was 1.25%. Reaction time at 25° C. is one hour after which excess glutaraldehyde was removed by efficient overnight dialysis at 4° C. against 0.1 molar sodium chloride in the same phosphate buffer as above. In a second step an excess of the biochemical compound (e.g., monoclonal antibody or DNA probe containing a primary amino group) is reacted with the glutaraldehyde activated microparticles for five hours at 25° C. In some experiments a longer reaction time and higher pH yields superior coupling. The excess reactants are removed by repeated centrifugation and washing with the phosphate buffered saline, at pH 7.0. Alternative methods for removing the excess reagents have already been discussed.

In some applications it is desirable to use partially polymerized glutaraldehyde rather than freshly purified monomers since this provides a longer molecular arm on the microparticles and access to the complementary target molecules is thereby increased.

There are numerous alternative methods for chemically bonding biochemical compounds to polymeric materials.

It should be emphasized that the scope of this invention includes all uses of daylight fluorescent molecules to detect biological molecules. It bears emphasis that this includes the use of daylight fluorescent materials in any reaction wherein a molecule to be detected originates in a living organism or such a molecule is used to detect another molecule. For example, antibody molecules can be used to detect a variety of molecules of synthetic origin (Fudenberg, Sites, Caldwell and Wells, *Basic and Clinical Immunology* (1976)), as well as molecules generated by living organisms. Synthetic DNA probes may be used to detect specific sequences of natural DNA.

Although in this discussion and in the examples that follow the terms antigen and antibody have been used, these terms are unduly restrictive. An antibody can be recognized as an antigen by another antibody. Also, in an assay system, an antibody can be detected by allowing it to bind to a molecule which is antigenic for it and which is immobilized on the surface of a microparticle. In order to discuss the present invention in the most general terms, the term immunological ligand will be used as a substitute for antigen and antibody.

The assays described below are adaptable to the detection of hormones, neurotransmitters and their receptors, as well as for nucleic acid strands containing particular coding sequences.

EXAMPLE 1

A pattern of small blind holes or wells, each several millimeters in diameter, are machined or molded into one end, of a small plastic dipstick. A different immunological ligand (or a different concentration of such ligand) is then bonded to the bottom of each small well using methods already described for bonding biochemical compounds to polymers. The stick is then dipped into suitably diluted human serum which is thought to contain antibodies directed against one or more of the antigens now present in different wells of the dipstick. After a suitable reaction period which is normally 5 or 10 minutes, the dipstick is removed and excess serum is washed off. If the human serum being tested contained immunological ligands directed against any one of the immunological ligands present in the wells of the dipstick, those wells will now be coated with human immunological ligands. Purified goat antibodies, specific for human antibodies, are labeled with daylight fluorescent polymers, and are allowed to react with each of the wells on the dipstick. Again, after a suitable reaction time of 5 or 10 minutes, the excess reagent is washed away and the stick is examined for the presence of intense daylight fluorescence in any of the wells. In a test of this type it is often possible and satisfactory simply to examine the stick with the eye and note which wells are colored. This then indicates the presence of antibodies in the serum which are directed against the antigens of interest

EXAMPLE 2

A dipstick prepared as in Example 1 in which a series of wells are coated with different concentration an immunological ligand, and a semi-quantitative result is obtained by noting each color in the well as compared with a reference.

EXAMPLE 3

A dipstick prepared as in Example 1 and in which each of the wells is precoated with a pigment of different color than that attached to the second immunological ligand. Thus yellow wells change to various shades of orange or red when red daylight fluorescent labels are bound. A semi-quantitative indication of the concentration of molecules in the test solution can be obtained by comparing the color of the wells with the color of a reference chart.

Ordinary fluorescent as well as daylight fluorescent pigments may be used as labels in this assay.

EXAMPLE 4

Immunoabsorbant purified goat anti-human chorionic gonadotropin (HCG) is coated in the form of an alphanumeric symbol such as a plus sign on a small, round, plastic disc. A preferred form of the disc is a macroporous, honeycomb or convoluted surface which has a greatly increased surface area. In one preferred form of this test the remainder of the disc surrounding the plus sign is coated with goat antibody which is not reactive with HCG. In order to detect the presence of HCG (i.e., a pregnancy test) the disc is allowed to react with a sample of human urine or serum. The disc is also allowed to react with a monoclonal antibody labeled with daylight fluorescent polymers, and which is directed against the beta chain of HCG. This reaction can either occur simultaneously with the incubation with the urine or serum, or in a subsequent step. The HCG serves as a bridge, binding the daylight fluorescent label to the surface of the plastic disc. After the excess reagent is rinsed away, the disc is examined under ordinary light or filtered, light of the appropriate wavelengths. In many cases, UV light can also be used. If a colored-plus sign is seen, this indicates the presence of HCG in the sample tested. If no daylight fluorescence is seen, no HCG was present in the amount measurable by the assay. On the other hand, if the disc is completely colored, a false positive reaction is indicated because the region outside the plus sign was coated with the nonreactive goat antibody control. This new type of pregnancy test greatly minimizes one of the most serious difficulties normally encountered in pregnancy tests, namely false positive results in a finite percentage of the cases. It also reduces the subjective judgment needed in detecting a positive or negative result since a pattern (such as a plus sign) is present only in the case of a true positive reaction.

A variety of pigments, including ordinary fluorescent ones, chemiluminescent and electroluminescent pigments, and phosphorescent pigments may be used as labels in place of daylight fluorescent pigments.

EXAMPLE 5

A honeycomb sponge or other high surface area material is contained within a cartridge capable of holding a test solution. Immunological ligands which bind the molecule to be assayed are bound to the surface of the material in the cartridge. These ligands are then saturated with a purified sample of the molecule to be assayed, or its analog. In either case the molecule used to saturate the binding sites is covalently bound to fluorescent particles. This sponge or honeycomb is then thoroughly washed and then dried in the presence of preserving material such as dilute glycerol or polymeric compounds which are utilized to stabilize the reagent. The honeycomb or sponge-like cartridge is used to absorb the test specimen which fills the volume of the cartridge. If the test sample contains the molecule sought it competes for the binding sites occupied by fluorescent labeled molecules. Thus when the sponge is exposed to the test solution the molecules sought to be assayed will compete for the binding sites on the sponge and cause the daylight fluorescent labeled particles to be free in solution. At the end of reaction period the labeled reagents which have been freed by reaction with the test solution are eluted from the cartridge and read quantitatively in a simple instrument which monitors the fluorescence emission.

EXAMPLE 6

An assay as described in Example 5 where the material covalently bound to the sponge or honeycomb is a nucleic acid strand complementary to the nucleic acid sought to be assayed, and in which these sites are preabsorbed with nucleic acid strands similar or identical in base sequence to those sought to be assayed, and are covalently bound to a daylight fluorescent material.

Although six specific embodiments of the present invention have been presented in detail, other alternatives will be apparent to one skilled in this art. Accordingly, the embodiments discussed should be viewed as examples of the claimed invention rather than limitations.

What is claimed is:

1. A method for assaying biological molecules comprising a support to which are bound on a portion of the surface of said support first molecules complementary to second molecules, said second molecules being said biological molecules, the balance of the surface of said support having bound thereto third molecules which are similar to the first molecules but not complementary to second molecules, the third molecules being attached to a portion of the support, and fourth molecules, also complementary to the second molecules, and labeled with a daylight fluorescent pigment, and causing the fourth molecules to become attached to those second molecules bound to first molecules.

2. The method of claim 1 wherein the assay is a pregnancy test, said second molecules are human chorionic gonadotropin, said fourth molecules cause daylight fluorescence only on said portion of the surface when human chorionic gonadotropin is present.

3. A method for assaying biological molecules according to claim 1 in which the substrate has a convoluted surface.

4. A method according to claim 1 in which the complementary molecule is an immunological ligand.

5. A method according to claim 1 in which the complementary molecule is a nucleic acid.

6. A method according to claim 1 in which the complementary molecule is one of a ligand receptor pair.

7. A method for assaying of biological molecules in which first molecules, complementary to the biological molecules which are to be assayed, are bound to a surface dyed with a first color, the method comprising the steps of:

(a) exposing the surface coated with the first molecule to an unknown solution thought to contain second molecules, said second molecules being biological molecules which are to be assayed.

(b) adding to this solution daylight fluorescent pigmented microparticles which have been coated with third molecules also complementary to the second molecules which are to be assayed; and (c) comparing the resulting color with a predetermined list of colors and corresponding concentrations of the second molecules, to obtain an indication of the concentration of the second molecules.

8. A method according to claim 7 in which the labeled molecules are immunological ligands.

9. A method according to claim 7 in which the labeled molecules are nucleic acids.

10. A method according to claim 7 in which each of the labeled molecules is a receptor of the first molecules.

11. A method according to claim 7 in which the substrate to which the first molecules are bound have a convoluted surface.

12. A method for assaying of biological molecules in which a plurality of first molecules complementary to a second molecule to be assayed are bound to the surface of a convoluted support in a container in which a plurality of third molecules which are the second molecules or analogues thereof are bound to the first molecules, said second molecules being biological molecules, and in which the third molecules are covalently bound to the surfaces of daylight fluorescent pigmented microparticles, the method comprising the steps of:

(a) exposing first and third molecules to an aqueous solution containing second molecules to be assayed, (b) allowing second molecules to bind to the first molecules; and (c) determining the number of third molecules released from said surface.

13. A method according to claim 12 in which the first, the second, and the third molecules are immunological ligands.

14. A method according to claim 12 in which the first, the second, and the third molecules are nucleic acids.

15. A method for assaying first biological molecules comprising labeling second molecules which are complementary to the first biological molecules with microparticles exhibiting daylight fluorescence, and causing the labeled second molecules to contact the first biological molecules.

16. A method of labeling cells by contacting cells with molecules bound to microparticles exhibiting daylight fluorescence.

17. A method for assaying of biological molecules in which first molecules, complementary to the biological molecules which are to be assayed, are bound to a dipstick comprising a substrate containing a plurality of discrete areas therein, each of said areas having bonded to the surface thereof said first molecules, said method comprising:

(a) contacting said dipstick into a specimen thought to contain said biological molecules, (b) contacting the dipstick with third molecules labeled with a daylight fluorescent pigment, said third molecule being complementary to the biological molecules, and (c) examining the dipstick for presence of daylight fluorescence in any of said areas.

* * * * *